United States Patent
Taub

(10) Patent No.: US 12,303,503 B1
(45) Date of Patent: May 20, 2025

(54) USE OF DEXTROMETHORPHAN IN COMBINATION WITH CYP2D6 AND CYP3A4 ENZYME INHIBITORS FOR THE TREATMENT OF PAIN

(71) Applicant: BIOBINA LLC, New York, NY (US)

(72) Inventor: Robert Taub, New York, NY (US)

(73) Assignee: BIOBINA LLC, New York, NY (US)

( * ) Notice: Subject to any disclaimer, the term of this patent is extended or adjusted under 35 U.S.C. 154(b) by 0 days.

(21) Appl. No.: 18/510,882

(22) Filed: Nov. 16, 2023

(51) Int. Cl.
*A61K 31/485* (2006.01)
*A61K 31/366* (2006.01)
*A61K 31/4748* (2006.01)
*A61K 45/06* (2006.01)
*A61P 25/04* (2006.01)

(52) U.S. Cl.
CPC .......... *A61K 31/485* (2013.01); *A61K 31/366* (2013.01); *A61K 31/4748* (2013.01); *A61K 45/06* (2013.01); *A61P 25/04* (2018.01)

(58) Field of Classification Search
CPC ................ A61K 31/485; A61K 31/366; A61K 31/4748; A61P 25/04
See application file for complete search history.

(56) References Cited

U.S. PATENT DOCUMENTS

| | | | |
|---|---|---|---|
| 4,785,055 A | 11/1988 | Dexter et al. | |
| 5,863,927 A | 1/1999 | Smith et al. | |
| 5,948,433 A | 9/1999 | Burton et al. | |
| 5,985,311 A | 11/1999 | Cordes et al. | |
| 6,207,674 B1 | 3/2001 | Smith | |
| 6,461,644 B1 | 10/2002 | Jackson et al. | |
| 6,676,961 B1 | 1/2004 | Lichter | |
| 8,569,328 B1 * | 10/2013 | Tabuteau | A61K 31/485 514/281 |
| 8,906,647 B2 | 12/2014 | Eissenstat et al. | |
| 9,540,354 B2 | 1/2017 | Eissenstat et al. | |
| 2012/0046262 A1 | 2/2012 | Davis | |
| 2020/0316056 A1 | 10/2020 | James et al. | |
| 2020/0376086 A1 | 12/2020 | Jankowski et al. | |

FOREIGN PATENT DOCUMENTS

| | | | | |
|---|---|---|---|---|
| IN | 434627 B | 6/2023 | | |
| WO | WO-2006024018 A2 * | 3/2006 | ............. | A61K 31/13 |
| WO | 2020190971 A1 | 9/2020 | | |
| WO | 2023036473 A1 | 3/2023 | | |

OTHER PUBLICATIONS

Nguyen, Linda, et al., "Involvement of sigma-1 receptors in the antidepressant-like effects of dextromethorphan," PloS one, Feb. 2014, e89985, 9.2.
Shin, Seung Min, et al., "Sigma-1 receptor activity in primary sensory neurons is a critical driver of neuropathic pain," Gene therapy, Feb. 2022, pp. 1-15, 29.1-2.
Lauterbach, Edward C., "Dextromethorphan as a potential rapid-acting antidepressant," Medical hypotheses, May 2011, pp. 717-719, 76.5.
Hirshberg, R. M., et al., "Is there a pathway in the posterior funiculus that signals visceral pain?," Pain, Oct. 1996, pp. 291-305, 67.2-3.
Nauta, Haring JW, et al., "Punctate midline myelotomy for the relief of visceral cancer pain," Journal of Neurosurgery: Spine, Apr. 2000, pp. 125-130, 92.2.
Gerber, Urs, Christine E. Gee, and Pascal Benquet, "Metabotropic glutamate receptors: intracellular signaling pathways," Current opinion in pharmacology, Feb. 2007, pp. 56-61, 7.1.
Wiesenfeld-Hallin, Zsuzsanna, and Xiao-Jun Xu, "Neuropeptides in neuropathic and inflammatory pain with special emphasis on cholecystokinin and galanin," European journal of pharmacology, Oct. 2001, pp. 49-59, 429.1-3.
Pan, Hui-Lin, et al., "Modulation of pain transmission by G-protein-coupled receptors," Pharmacology & therapeutics, Jan. 2008, pp. 141-161, 117.1.
Shaibani, Aziz I., et al., "Efficacy and safety of dextromethorphan/ quinidine at two dosage levels for diabetic neuropathic pain: a double-blind, placebo-controlled, multicenter study," Pain medicine, Feb. 2012, pp. 243-254, 13.2.
Stahl, Stephen M., "Mechanism of action of dextromethorphan/ quinidine: comparison with ketamine," CNS spectrums, Oct. 2013, pp. 225-227, 18.5.
Flockhart DA, Thacker, D., McDonald, C., Desta, Z. The Flockhart Cytochrome P450 Drug-Drug Interaction Table. Division of Clinical Pharmacology, Indiana University School of Medicine (Updated 2021). https://drug-interactions.medicine.iu.edu/. Accesed Nov. 20, 2023, 2 pages.
Leeder, J. Steven, "Pharmacogenetics and pharmacogenomics," Pediatric Clinics of North America, Jun. 2001, pp. 765-782, 48.3.

(Continued)

*Primary Examiner* — Kevin E Weddington
(74) *Attorney, Agent, or Firm* — Carter, DeLuca & Farrell LLP; Jeffrey S. Steen; George Likourezos

(57) ABSTRACT

Methods and compositions for treating pain are provided. Methods for treating pain include administering an effective amount of dextromethorphan or a pharmaceutically acceptable salt thereof in combination with a CYP2D6 enzyme inhibitor and a CYP3A4 enzyme inhibitor to a subject in need thereof. Compositions for treating pain that include dextromethorphan or a pharmaceutically acceptable salt thereof in combination with a CYP2D6 enzyme inhibitor and a CYP3A4 enzyme inhibitor are administered to a subject in need thereof.

29 Claims, No Drawings

(56) References Cited

OTHER PUBLICATIONS

Taylor, Charles P., et al., "Pharmacology of dextromethorphan: Relevance to dextromethorphan/quinidine (Nuedexta®) clinical use," Pharmacology & therapeutics, Aug. 2016, pp. 170-182, 164.
Strauch, Katja, et al., "Dose-response relationship for the pharmacokinetic interaction of grapefruit juice with dextromethorphan investigated by human urinary metabolite profiles," Food and chemical toxicology, Aug. 2009, pp. 1928-1935, 47.8.
Anonymous, WebMD-Grapefruit Interactions, Feb. 1, 2023, https://www.webmd.com/vitamins/ai/ingredientmono-946/grapefruit, 1 page.
Anonymous, "Drug Interactions," Nuedexta, Feb. 3, 2023, https://www.rxlist.com/nuedexta-drug.htm#interactions, 1 page.
Romero, L., et al., "Pharmacological properties of S1RA, a new sigma-1 receptor antagonist that inhibits neuropathic pain and activity-induced spinal sensitization," British journal of pharmacology, Aug. 2012, pp. 2289-2306, 166.8.
Anonymous, "Highlights of Prescribing Information," Avanir Pharmaceuticals, Inc., Oct. 2010, 19 pages.
Majeed, Amna, et al., "Efficacy of dextromethorphan for the treatment of depression: a systematic review of preclinical and clinical trials," Expert Opinion on Emerging Drugs, Jan. 2021, pp. 63-74, 26.1.
Lisak, Robert P., Liljana Nedelkoska, and Joyce A. Benjamins, "Effects of dextromethorphan on glial cell function: proliferation, maturation, and protection from cytotoxic molecules," Glia, May 2014, pp. 751-762, 62.5.
Ye, Lin-Hu, et al., "Lotus leaf alkaloid fraction can strongly inhibit CYP2D6 isoenzyme activity," Journal of ethnopharmacology, Dec. 2016, pp. 913-917, 194.
Nguyen, Linda, et al., "Dextromethorphan: an update on its utility for neurological and neuropsychiatric disorders," Pharmacology & therapeutics, Mar. 2016, pp. 1-22, 159.
Merlos, Manuel, et al., "Sigma-1 receptor and pain," Sigma Proteins: Evolution of the Concept of Sigma Receptors (2017): 131-161.
Asokan, Shibu Marthandam, et al., "Pharmacological benefits of neferine-A comprehensive review," Life sciences, Apr. 2018, pp. 60-70, 199.
Su, Tsung-Ping, et al., "The sigma-1 receptor as a pluripotent modulator in living systems," Trends in pharmacological sciences, Apr. 2016, pp. 262-278, 37.4.
Brooks, B. R., et al., "Treatment of pseudobulbar affect in ALS with dextromethorphan/quinidine: a randomized trial," Neurology, Oct. 2004, pp. 1364-1370, 63.8.
International Search Report for application No. PCT/US2024/055822, Feb. 25, 2025, 18 pages.

\* cited by examiner

USE OF DEXTROMETHORPHAN IN COMBINATION WITH CYP2D6 AND CYP3A4 ENZYME INHIBITORS FOR THE TREATMENT OF PAIN

TECHNICAL FIELD

Treatment of pain with dextromethorphan and CYP2D6 and CYP3A4 enzyme inhibitors.

BACKGROUND

Pain may be defined as a localized or generalized unpleasant bodily sensation or complex of sensations that causes mild to severe discomfort and emotional distress. According to the National Institutes of Health, National Institute of Neurological Disorders and Stroke, pain can be classified as acute or chronic. As used herein the term "pain" is meant to include acute pain, chronic pain, nociceptive pain, neuropathic pain, psychogenic pain, breakthrough pain and intractable pain.

Acute pain usually results from a specific injury, disease, and/or inflammation. It generally appears suddenly, for example, after physical trauma or surgery, and can be accompanied by anxiety or emotional distress. Acute pain may be a protective response to tissue damage resulting from injury, disease, overuse, or environmental stressors. Normally, acute pain is self-limiting, i.e., it is confined to a given period of time and severity. Acute pain, however, can become chronic.

Chronic pain persists over a long period and can be challenging to manage. People with chronic pain may often suffer from more than one painful condition. They can also have an increased risk for developing problems with physical functioning, cognition, and emotional reactions.

Nociceptive pain is discomfort caused by damage or injury to non-neural tissue and is due to the activation of a nociceptor. Nociceptors are specialized sensory nerve cells or neurons throughout the body that trigger a series of responses to a noxious (painful) stimulus. The stimulus triggers an electrical impulse that travels through nerves from the site of the injury or diseased area to the spinal cord and up to the brain.

Neuropathic pain is defined by the International Association for the Study of Pain (IASP) as pain caused by a lesion or disease of the somatosensory nervous system. Chronic neuropathic pain is a consequence of injury or disease affecting the somatosensory system that persists for more than three months, often after the cause is no longer active. According to the IASP, at least 7% to 10% of the general population suffers from neuropathic pain, although prevalence may be underestimated. Treatment remains suboptimal because traditional drugs including opiates provide only modest and often tachyphylactic pain relief.

Psychogenic pain is physical pain that is caused, increased, or prolonged by mental, emotional, or behavioral factors, without evidence of physical injury or illness. Headache, back pain, or stomach pain are some of the most common types of psychogenic pain. It is commonly accompanied by social rejection, a broken heart, grief, lovesickness, regret, or other such emotional events. Psychogenic pain can also be caused by psychological disorders such as anxiety and depression, which can affect the onset and severity of pain experienced.

Breakthrough pain refers to a transitory flare-up of pain in the context of existing therapy that has been controlling baseline pain.

Intractable pain is a severe, constant, relentless and debilitating pain that is difficult to treat or manage. Intractable pain is not curable by any known means and is often constant and agonizing. The pain can be so excruciating that eating and sleeping are affected. It may cause a house-bound or bed-bound state and early death if not adequately treated, usually with opioids and/or interventional procedures. It is typically not relieved by ordinary medical, surgical, nursing, or pharmaceutical measures.

The traffic of chemical impulses between subpopulations of primary afferent neurons in the dorsal horn of the spinal cord, and their connections in the anterior cortical and hippocampal regions, underlies the experience of such pain regardless of how it is categorized. Pharmacologic systems thought to contribute to the transmission and modulation of pain signals between neurons may include the participation of over 60 identified coexisting neurochemicals and amino acids, notably receptors for N-methyl-D-aspartate (NMDA), norepinephrine and serotonin uptake, and the receptor termed sigma-1.

It has been demonstrated that the sigma-1 receptor subtype may be significantly involved in the perception and transmission of chronic neuropathic pain. See, e.g., Shin et al., Gene Ther. 2022 February; 29(1-2): 1-15. Sigma-1 receptor function and activity may be modulated by dextromethorphan (DXM), an opiate-related drug with promising but as yet poorly understood analgesic properties. Cf. Nguyen et al., (2014) Involvement of Sigma-1 Receptors in the Antidepressant-like Effects of Dextromethorphan. PLoS ONE 9(2): e89985.

Dextromethorphan was first developed as one of the two enantiomers of methorphan as an antitussive (cough suppressant) at low doses and a dissociative agent at high doses. Dextromethorphan can possess significant analgesic activity. It is generally considered to have a lower potential for addiction compared to certain other analgesics such as opiates. Dextromethorphan is an active ingredient found in many over-the-counter cough and cold medications. Misuse or abuse of dextromethorphan, involving taking it in high doses (5-7 or more times the recommended doses or for recreational purposes), can lead to psychological and physical dependence. It can be used either alone or even to potentiate opiates. In contrast to opiates, dextromethorphan has relatively low toxicity and rarely results in death. Although there have been reported deaths from dextromethorphan overdose, they have almost invariably occurred in association with ingestion of other drugs, or by involvement in an accident (dextromethorphan can lead to impairment of the senses).

After dextromethorphan was developed, it was soon also used for postoperative pain relief with some success but was considered inadequate for treatment of chronic pain. As dextromethorphan is rapidly metabolized by the hepatic and intestinal cytochrome P450 enzyme 2D6 (CYP2D6), oral administration of dextromethorphan leads to rapid and unsustained peak levels of drug with a short duration of action, fully adequate for rapid-onset, short-duration antitussive actions. However, oral administration of dextromethorphan alone does not provide sustained levels needed to substantially occupy neurotransmitter receptors in the brain without frequent administration and high-peak doses that incur dissociative side effects. Dextromethorphan has therefore been combined with a low dose of the CYP2D6 inhibitor quinidine and converted into a twice-a-day formulation with over 20 times the therapeutic exposure to dextromethorphan levels compared to dextromethorphan alone. This drug combination largely avoids the high peak levels that can cause dissociative reactions yet provides the drug levels necessary for consistent receptor occupancy over time. Pain relief by dextromethorphan plus quinidine has been observed in placebo controlled trials and the combination of dextromethorphan plus quinidine sulfate is currently FDA approved for treating episodes of pseudo-bulbar affect (PBA). However, the pain relief caused by dextromethorphan plus quinidine has been found to be temporary within the chronic pain context, i.e., pain can return within one to three weeks.

The pharmacologic actions of dextromethorphan are currently thought to involve a relatively weak mu-1 opiate receptor binding property, a modest NMDA receptor antagonism (as compared with ketamine), a more potent, perhaps most significant sigma 1 action, as well as a potent serotonin reuptake binding inhibitory property. Which receptor or combination of receptors mediate(s) the therapeutic action of dextromethorphan in PBA is unknown. Currently, dextromethorphan is the only non-FDA regulated drug with significant activity against the Si-receptor.

As noted above dextromethorphan is mainly metabolized to dextrorphan by CYP2D6, which is present in both liver and intestinal tract. This enzyme is not considered to be readily inducible. Dextromethorphan is also metabolized to a minor degree to dextrorphan and to 3-methoxymorphinan by the more versatile CYP3A4, an enzyme which is readily inducible by pregnancy and many drugs.

In many instances pharmacologic treatments for pain may offer some relief but are far from a panacea. The hazards of opiate treatment are well-known. Addiction resulting from chronic administration of opiates has become a national and global scourge. Chronic corticosteroid administration may cause increased appetite and weight gain, changes in mood, muscle weakness and Cushing syndrome. Non-steroidal anti-inflammatory drugs are associated with side-effects such as stomach ulcers and tinnitus. Analgesics such as acetaminophen may cause liver damage. There remains a need for additional pharmaceutical therapies to treat pain.

SUMMARY

Methods and compositions for treating pain are provided. In embodiments, methods for treating pain include administering an effective amount of dextromethorphan or a pharmaceutically acceptable salt thereof in combination with a CYP2D6 enzyme inhibitor and a CYP3A4 enzyme inhibitor to a subject in need thereof. In embodiments, compositions for treating pain are provided that include dextromethorphan or a pharmaceutically acceptable salt thereof in combination with a CYP2D6 enzyme inhibitor and a CYP3A4 enzyme inhibitor that can be administered to a subject in need thereof. In embodiments, the compositions for treating pain may be administered enterally or parenterally.

In embodiments, the amount of dextromethorphan or a pharmaceutically acceptable salt thereof ranges from about 10 mg to about 200 mg. In embodiments, a composition containing dextromethorphan or a pharmaceutically acceptable salt thereof in combination with a CYP2D6 enzyme inhibitor and a CYP3A4 enzyme inhibitor is a conventional release composition. In embodiments, a composition containing dextromethorphan or a pharmaceutically acceptable salt thereof in combination with a CYP2D6 enzyme inhibitor and a CYP3A4 enzyme inhibitor is an extended release composition. In embodiments, a composition containing dextromethorphan or a pharmaceutically acceptable salt thereof in combination with a CYP2D6 enzyme inhibitor and a CYP3A4 enzyme inhibitor is an instant release composition. In embodiments, dextromethorphan or a pharmaceutically acceptable salt thereof in combination with a CYP2D6 enzyme inhibitor and a CYP3A4 enzyme inhibitor is administered to a subject in need thereof from one to four times daily.

In embodiments, methods for treating pain include administering an effective amount of dextromethorphan or a pharmaceutically acceptable salt thereof in combination with a CYP2D6 enzyme inhibitor and methocarbamol to a subject in need thereof. In embodiments, methods for treating pain include administering an effective amount of dextromethorphan or a pharmaceutically acceptable salt thereof in combination with a CYP2D6 enzyme inhibitor, methocarbamol and a CYP3A4 enzyme inhibitor to a subject in need thereof. In embodiments, compositions for treating pain are provided that include dextromethorphan or a pharmaceutically acceptable salt thereof in combination with a CYP2D6 enzyme inhibitor and methocarbamol that can be administered to a subject in need thereof. In embodiments, compositions for treating pain are provided that include dextromethorphan or a pharmaceutically acceptable salt thereof in combination with a CYP2D6 enzyme inhibitor, methocarbamol and a CYP3A4 enzyme inhibitor that can be administered to a subject in need thereof.

In embodiments, the amount of dextromethorphan or a pharmaceutically acceptable salt thereof ranges from about 10 mg to about 200 mg in combination with a CYP2D6 enzyme inhibitor and methocarbamol. In embodiments, the amount of dextromethorphan or a pharmaceutically acceptable salt thereof ranges from about 10 mg to about 200 mg in combination with a CYP2D6 enzyme inhibitor, methocarbamol and a CYP3A4 enzyme inhibitor. In embodiments, a composition containing dextromethorphan or a pharmaceutically acceptable salt thereof in combination with a CYP2D6 enzyme inhibitor, methocarbamol and optionally a CYP3A4 enzyme inhibitor is a conventional release composition. In embodiments, a composition containing dextromethorphan or a pharmaceutically acceptable salt thereof in combination with a CYP2D6 enzyme inhibitor, methocarbamol and optionally a CYP3A4 enzyme inhibitor is an extended release composition. In embodiments, a composition containing dextromethorphan or a pharmaceutically acceptable salt thereof in combination with a CYP2D6 enzyme inhibitor, methocarbamol and optionally a CYP3A4 enzyme inhibitor is an instant release composition. In embodiments, dextromethorphan or a pharmaceutically acceptable salt thereof in combination with a CYP2D6 enzyme inhibitor, methocarbamol and optionally a CYP3A4 enzyme inhibitor is administered to a subject in need thereof from one to four times daily. In embodiments, the compositions for treating pain may be administered enterally or parenterally.

In embodiments, the pain is chronic pain. In embodiments, the pain is acute pain. In embodiments, the pain is nociceptive pain. In embodiments, the pain is neuropathic pain. In embodiments, the pain is psychogenic pain. In embodiments, the pain is breakthrough pain. In embodiments, the pain is intractable pain.

DETAILED DESCRIPTION

Methods and compositions for treating pain are provided. In accordance with the present disclosure methods and compositions for treating pain are provided that relieve pain symptoms for prolonged duration without certain unwanted side effects associated with commonly prescribed medications for pain. In embodiments, methods for treating pain include administering an effective amount of dextromethorphan or a pharmaceutically acceptable salt thereof in combination with a CYP2D6 enzyme inhibitor and a CYP3A4 enzyme inhibitor to a subject in need thereof. In embodiments, compositions for treating pain that include dextromethorphan or a pharmaceutically acceptable salt thereof in combination with a CYP2D6 enzyme inhibitor and a CYP3A4 enzyme inhibitor are administered to a subject in need thereof.

The combination of dextromethorphan or a pharmaceutically acceptable salt thereof along with a CYP2D6 enzyme inhibitor and a CYP3A4 enzyme inhibitor overcomes the relatively short duration of action associated with administration of dextromethorphan or a pharmaceutically acceptable salt thereof and a CYP2D6 enzyme inhibitor alone. Without wishing to be bound by any particular theory, although a CYP2D6 enzyme inhibitor, e.g., quinidine, prevents metabolism of dextromethorphan when they are co-administered, CYP3A4 is eventually induced resulting in dextromethorphan metabolism and cessation of activity. If dextromethorphan is co-administered with only a CYP3A4 enzyme inhibitor, dextromethorphan is rapidly metabolized by CYP2D6 and is thus rendered ineffective for pain relief. Accordingly, the combination of dextromethorphan with a CYP2D6 enzyme inhibitor and a CYP3A4 enzyme inhibitor is a remarkable synergistic combination resulting in pain relief for prolonged duration.

The combination of dextromethorphan or a pharmaceutically acceptable salt thereof along with a CYP2D6 enzyme inhibitor and a CYP3A4 enzyme inhibitor provides prolonged and effective pain relief without the addiction potential of opiates or the side effects associated with non-steroidal anti-inflammatory medications (NSAIDs) or the side effects associated with corticosteroids. Accordingly, patients who are prescribed opiates, corticosteroids or NSAIDs can avoid, or receive lower doses of these medications when they are co-administered with a combination of dextromethorphan or a pharmaceutically acceptable salt thereof along with a CYP2D6 enzyme inhibitor and a CYP3A4 enzyme inhibitor. For patients who have become addicted to opiates, the combination of dextromethorphan or a pharmaceutically acceptable salt thereof along with a CYP2D6 enzyme inhibitor and a CYP3A4 enzyme inhibitor provides an effective modality for weaning off the opiates.

In embodiments, methods for treating pain include administering an effective amount of a combination of dextromethorphan or a pharmaceutically acceptable salt thereof along with a CYP2D6 enzyme inhibitor and a CYP3A4 enzyme inhibitor to a subject in need thereof. In embodiments, compositions for treating pain which include a combination of dextromethorphan or a pharmaceutically acceptable salt thereof along with a CYP2D6 enzyme inhibitor and a CYP3A4 enzyme inhibitor are administered to a subject in need thereof. In embodiments, methods of treating pain include administering a combination of dextromethorphan or a pharmaceutically acceptable salt thereof along with a CYP2D6 enzyme inhibitor and a CYP3A4 enzyme inhibitor to a subject in need thereof to provide pain relief in the subject.

In embodiments, the pain is chronic pain. In embodiments, the pain is acute pain. In embodiments, the pain is nociceptive pain. In embodiments, the pain is neuropathic pain. In embodiments, the pain is psychogenic pain. In embodiments, the pain is breakthrough pain. In embodiments, the pain is intractable pain. The pain can be from any source, e.g., patients with sickle cell anemia frequently experience pain which is difficult to control.

In embodiments, the CYP2D6 inhibitor may be one or more of quinidine, quinine, ajmaline, amiodarone, buprenorphine, bupropion, cannabidiol, celecoxib, chlorphenamine, chlorpromazine, cimetidine, cinacalcet, citalopram, clemastine, clomipramine, cocaine, diphenhydramine, doxepin, doxorubicin, duloxetine, escitalopram, fluoxetine, halofantrine, haloperidol, hydroxyzine, hyperforinkava, levomepromazine, lobeline, methadone, methylphenidate, metoclopramide, mibefradil, midodrine, niacin, niacinamide, *Nelumbo nucifera*, nuciferine, n-nornuciferine, 2-hydroxy-1-methoxyaporphine, omeprazole, paroxetine, perphenazine, promethazine, ranitidine, risperidone, ritonavir, sertraline, St. John's Wort, terbinafine, thioridazine, ticlopidine, tripelennamine, yohimbine and zuclopenthixol.

In embodiments, the CYP3A4 inhibitor may be one or more of amiodarone, aprepitant, atazanavir, bergamottin, 6'7' dihydoxybergamottin, buprenorphine, cafestol, cannabidiol, chloramphenicol, cimetidine, ciprofloxacin, clarithromycin, cobicistat, darunavir, delavirdine, diltiazem, dithiocarbamate, domperidone, erythromycin, esomeprazole, fluconazole, fluvoxamine, gestodene, *Ginkgo biloba*, grapefruit juice, imatinib, indinavir, isoniazid, itraconazole, kava, ketoconazole, lopinavir, mibefradil, mifepristone, milk thistle, myricetin, nefazodone, nelfinavir, niacin, niacinamide, nilutamide, norfloxacin, omeprazole, orphenadrine, pantoprazole, piperine, quercetin, ranitidine, ritonavir, saquinavir, seproxetine, star fruit, teliromycin, tipranavir, valerian, valproic acid, verapamil and voriconazole.

In embodiments, the terms "effective amount" or "therapeutically effective amount" may be used interchangeably and refer to an amount of a compound, material, composition, medicament, or other material that is effective to achieve reduction, elimination or prophylaxis of pain with a minimum of side effects normally associated with pain-relieving drugs.

In embodiments, an effective amount of dextromethorphan or a pharmaceutically acceptable salt thereof is between about 10 mg to about 200 mg from one to four times daily.

In embodiments, dextromethorphan may be provided as an acid addition salt, a zwitter ion hydrate, zwitter ion anhydrate, hydrochloride or hydrobromide salt. Acid addition salts, include but are not limited to, maleic, fumaric, benzoic, ascorbic, succinic, oxalic, bis-methylenesalicylic, methanesulfonic, ethane-disulfonic, acetic, propionic, tartaric, salicylic, citric, gluconic, lactic, malic, mandelic, cinnamic, citraconic, aspartic, stearic, palmitic, itaconic, glycolic, pantothenic, p-amino-benzoic, glutamic, benzene sulfonic or theophylline acetic acid addition salts, as well as the 8-halotheophyllines, for example 8-bromo-theophylline. In embodiments, inorganic acid addition salts, including but not limited to, hydrochloric, hydrobromic, hydroiodic, sulfuric, sulfamic, phosphoric or nitric acid addition salts may be used.

In embodiments, an effective amount of quinidine is about 20 to about 300 mg, quinine about 20 to 300 mg, ajmaline about 25 mg to about 200 mg, amiodarone about 20 to about 400 mg, buprenorphine about 5 mg to about 25 mg, bupropion about 50 mg to about 450 mg, cannabidiol about 50 mg to about 1500 mg, celecoxib about 25 mg to about 250 mg, chlorphenamine about 2 mg to about 15 mg, chlorpromazine about 5 mg to about 75 mg, cimetidine about 100 mg to about 1000 mg, cinacalcet about 5 mg to about 500 mg, citalopram about 5 mg to about 75 mg, clemastine about 0.5 mg to about 10 mg, clomipramine about 5 mg to about 400 mg, cocaine, diphenhydramine about 10 mg to about 100 mg, doxepin about 10 mg to about 400 mg, doxorubicin about 30 to about 70 mg/m2, duloxetine about 5 mg to about 75 mg, escitalopram about 1 mg to about 50 mg, fluoxetine about 5 mg to about 150 mg, halofantrine about 100 mg to about 1000 mg, haloperidol about 0.1 mg to about 30 mg, hydroxyzine about 5 mg to about 100 mg, hyperforinkava about 100 mg to about 1000 mg, levomepromazine about 5 mg to about 75 mg, lobeline about 10 mg to about 500 mg, methadone about 5 mg to about 150 mg, methylphenidate about 1 mg to about 75 mg, metoclopramide about 1 mg to about 20 mg, mibefradil about 10 mg to about 150 mg, midodrine about 1 mg to about 20 mg, niacin about 10 mg to about 2000 mg, niacinamide about 10 mg to about 2000 mg, *Nelumbo nucifera* about 10 mg/kg to about 500 mg/kg, nuciferine about 10 mg/kg to about 500 mg/kg, n-nornuciferine about 10 mg/kg to about 500 mg/kg, 2-hydroxy-1-methoxyaporphine about 0.1 mg to about 10 mg, omeprazole about 1 mg to about 75 mg, paroxetine about 5 mg to about 100 mg, perphenazine about 2 mg to about 20 mg, promethazine about 5 mg to about 50 mg, ranitidine about 10 mg to about 400 mg, risperidone about 0.1 to about 10 mg, ritonavir about 10 mg to about 750 mg, sertraline about 10 mg to about 400 mg, St. John's Wort about 100 mg to about 2000 mg, terbinafine about 50 mg to about 500 mg, thioridazine about 10 mg to about 1000 mg, ticlopidine about 50 mg to about 500 mg, tripelennamine about 5 mg to about 75 mg, yohimbine about 1 mg to about 50 mg and zuclopenthixol about 1 mg to about 250 mg. In the case of quinidine, doses should be set below levels that may increase the QTc interval, e.g., less than 50 mg every 6 hours.

In embodiments, an effective amount of amiodarone is about 25 mg to about 500 mg, aprepitant about 25 mg to about 200 mg, atazanavir about 100 mg to about 500 mg, bergamottin about 0.01 mg to about 20 mg, 6'7' dihydroxy-bergamottin about 0.01 mg to about 20 mg, buprenorphine about 5 mg to about 25 mg, cafestol about 1 mg to about 50 mg, cannabidiol about 50 mg to about 1500 mg, chloramphenicol about 10 mg to about 1000 mg, cimetidine about 100 mg to about 1000 mg, ciprofloxacin about 50 mg to about 1000 mg, clarithromycin about 75 mg to about 750 mg, cobicistat about 50 mg to about 200 mg, darunavir about 100 mg to about 1000 mg, delavirdine about 25 mg to about 500 mg, diltiazem about 25 mg to about 60 mg, dithiocarbamate, domperidone about 1 mg to about 50 mg, erythromycin about 50 mg to about 1000 mg, esomeprazole about 5 mg to about 75 mg, fluconazole about 25 mg to about 750 mg, fluvoxamine about 5 mg to about 500 mg, gestodene about 10 mcg to about 500 mcg, *Ginkgo biloba* about 10 mg to about 1000 mg, grapefruit juice about 0.5 oz to about 25 oz, imatinib about 10 mg to about 800 mg, indinavir about 200 mg to about 1600 mg, isoniazid about 50 mg to about 500 mg, itraconazole about 50 mg to about 500 mg, kava, ketoconazole about 50 mg to about 500 mg, lopinavir about 50 mg to about 1000 mg, mibefradil about 10 mg to about 200 mg, mifepristone about 10 mg to about 500 mg, milk thistle about 5 mg to about 500 mg, myricetin about 1 mg to about 500 mg, nefazodone about 10 mg to about 750 mg, nelfinavir about 100 mg to about 2000 mg, niacin about 10 mg to about 2000 mg, niacinamide about 10 mg to about 2000 mg, nilutamide about 50 mg to about 500 mg, norfloxacin about 50 mg to about 900 mg, omeprazole about 1 mg to about 75 mg, orphenadrine about 10 mg to about 500 mg, pantoprazole about 5 mg to about 75 mg, piperine about 1 mg to about 50 mg, quercetin about 1 mg to about 1000 mg, ranitidine about 10 mg to about 400 mg, ritonavir about 10 mg to about 750 mg, saquinavir about 100 mg to about 2000 mg, seproxetine about 10 mg to about 200 mg, star fruit about 20 gm to about 500 gm as juice, tipranavir about 50 mg to about 1000 mg, valerian about 100 to about 1000 mg, valproic acid about 100 mg to about 2500 mg, verapamil about 50 mg to about 600 mg and voriconazole about 50 mg to about 500 mg.

It should be understood that the foregoing effective amounts are exemplary. Those skilled in the art can adjust the amounts upwardly or downwardly based on a subject's age, weight and condition. In embodiments, the combination of dextromethorphan or a pharmaceutically acceptable salt thereof along with a CYP2D6 enzyme inhibitor and a CYP3A4 enzyme inhibitor may be administered in one, two, three, four or more doses. In embodiments, the subject may be started at a low dose and the dosage is escalated over time.

As an example, a pharmaceutical composition for treatment of pain may include 30-60 mg dextromethorphan, 25-50 mg ritonavir and 0-25 mg quinidine incorporated into a solid or liquid form and given to a subject in need every 12 hours. Use of ritonavir which has dual inhibitory action on both CYP2D6 and CYP3A4, and a lack of cardiac toxicity at that dose, could allow dose reduction or outright elimination of the need for another CYP2D6 enzyme inhibitor such as quinidine which may cause arrhythmias.

In embodiments the combination of dextromethorphan or a pharmaceutically acceptable salt thereof along with a CYP2D6 enzyme inhibitor and a CYP3A4 enzyme inhibitor is administered to a subject experiencing pain via one or more pharmaceutical compositions. "Pharmaceutical compositions" and "compositions" are used interchangeably herein. Pharmaceutical compositions herein encompass dosage forms. Dosage forms herein encompass unit doses. In embodiments, as discussed below, various dosage forms including conventional formulations and modified release formulations can be administered one, two, three, four or more times daily. In embodiments, the combination of dextromethorphan or a pharmaceutically acceptable salt thereof along with a CYP2D6 enzyme inhibitor and a CYP3A4 enzyme inhibitor is administered to a subject once or twice a day, (e.g., morning and/or evening). In embodiments, the combination of dextromethorphan or a pharmaceutically acceptable salt thereof along with a CYP2D6 enzyme inhibitor and a CYP3A4 enzyme inhibitor is administered to a subject three times a day, (e.g., morning, afternoon and at bedtime, or every 8 hours). In embodiments, the combination of dextromethorphan or a pharmaceutically acceptable salt thereof along with a CYP2D6 enzyme inhibitor and a CYP3A4 enzyme inhibitor is administered to a subject four times a day, (e.g., morning, afternoon, evening and at bedtime, or every 6 hours). In embodiments, is administered to a subject at the start of a breakthrough pain episode, whenever that may occur.

In embodiments, the combination of dextromethorphan or a pharmaceutically acceptable salt thereof along with a CYP2D6 enzyme inhibitor and a CYP3A4 enzyme inhibitor may be co-administered with one or more additional NMDA receptor antagonists. Examples of NMDA receptor antagonists include amantadine, ketamine, esketamine, memantine, atomoxetine, agmatine, delucemine, dextrorphan, eliprodil, gabapentin and magnesium. The additional NMDA receptor antagonist(s) potentiate the analgesic effects of the combination of dextromethorphan or a pharmaceutically acceptable salt thereof along with a CYP2D6 enzyme inhibitor and a CYP3A4 enzyme inhibitor.

In embodiments, dextromethorphan or a pharmaceutically acceptable salt thereof in combination with a CYP2D6 enzyme inhibitor and methocarbamol. In embodiments, dextromethorphan or a pharmaceutically acceptable salt thereof in combination with a CYP2D6 enzyme inhibitor and a CYP3A4 enzyme inhibitor may be co-administered with methocarbamol. Methocarbamol is a skeletal muscle relaxant and a central nervous system depressant. As a treatment for involuntary skeletal muscle spasm, methocarbamol is considered an anti-spasmodic agent. The exact mechanism of action of methocarbamol remains unknown.

In embodiments, an effective amount of methocarbamol is between about 100 mg to about 2000 mg from one to four times daily. For example, a subject may be administered a dose of 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, or 2000 mg from one to four times daily. In embodiments, a subject may be administered from 500 mg to 9000 mg within 24 hours. For example, daily doses can range from four to eight grams daily in divided doses every six hours.

Methocarbamol is commercially available as 500 mg tablets, 700 mg tablets, 750 mg tablets and as an injectable solution of 100 mg/ml. In embodiments, adult parenteral doses of methocarbamol may be 1 g intravenously or intramuscularly (IV/IM); additional doses could be given at every 8 hours. In embodiments, methocarbamol may be administered from 500 mg to 1500 mg orally every 6 hours for 48-72 hours. A pediatric dose may be 15 mg/kg/dose IV every 6 hours as needed or a 500 mg/m$^2$/dose.

"Co-administered with", "administered in combination with", "a combination of", "the combination of", "administered along with", or "along with", may be used interchangeably and mean that two or more agents are administered in the course of therapy. The agents may be administered together at the same time or separately in spaced apart intervals. The agents may be administered in a single dosage form or in separate dosage forms. In embodiments, a CYP2D6 enzyme inhibitor or a CYP3A4 enzyme inhibitor or both may be administered prior to administration of dextromethorphan or a pharmaceutically acceptable salt thereof to allow enzyme inhibition to occur before the enzyme(s) have a chance to metabolize the dextromethorphan.

Any suitable route of administration may be utilized, e.g., enteral or parenteral including oral, rectal, nasal, pulmonary, vaginal, sublingual, buccal, transdermal, intravenous, intraarterial, epidural, intramuscular, intraperitoneal and subcutaneous routes. Suitable dosage forms include tablets, capsules, caplets, pills, oral liquids, lozenges, powders, films, aerosols, transdermal modalities such as topical liquids, patches, creams and ointments, parenteral formulations and suppositories. In embodiments, the combination of dextromethorphan or a pharmaceutically acceptable salt thereof along with a CYP2D6 enzyme inhibitor and a CYP3A4 enzyme inhibitor is used to manufacture a medicament for treatment of pain.

In embodiments, as mentioned previously, pharmaceutical compositions herein may be provided with conventional release or modified release profiles. Pharmaceutical compositions may be prepared using a pharmaceutically acceptable "carrier" composed of materials that are considered safe and effective. The "carrier" includes all components present in the pharmaceutical formulation other than the active ingredient or ingredients. The term "carrier" includes, but is not limited to, liquid vehicles, e.g., simple syrup, diluents, binders, lubricants, disintegrants, fillers, and coating compositions. Those with skill in the art are familiar with such pharmaceutical carriers and methods of compounding pharmaceutical compositions using such carriers. See, e.g., Remington: The Science and Practice of Pharmacy, 23rd Edition Academic Press (2020).

In embodiments, pharmaceutical compositions herein are modified release dosage forms which provide modified release profiles. Modified release dosage forms may exhibit immediate release, delayed release, or extended release profiles. Conventional (or unmodified) release dosage forms such as tablets, capsules, suppositories, syrups, elixirs, solutions and suspensions typically release medications into the mouth, stomach or intestines as the tablet, capsule shell or suppository dissolves, or, in the case of syrups, solutions and suspensions, when they are swallowed. The pattern of drug release from modified release (MR) dosage forms is deliberately changed from that of a conventional dosage form to achieve a desired therapeutic objective and/or better patient compliance. Types of MR drug products include orally disintegrating dosage forms (ODDFs) which provide immediate release, extended release dosage forms, delayed release dosage forms (e.g., enteric coated), and pulsatile release dosage forms.

An ODDF is a solid dosage form containing a medicinal substance or active ingredient which disintegrates rapidly, usually within a matter of seconds when placed upon or under the tongue. The disintegration time for ODDFs generally range from one or two seconds to about a minute. ODDFs are designed to disintegrate or dissolve rapidly on contact with saliva. This mode of administration can be beneficial to people who may have problems swallowing tablets whether it be from physical infirmity or psychiatric in nature. Subjects in pain may exhibit such behavior. ODDF's can provide rapid delivery of medication to the blood stream through mucosa resulting in a rapid onset of action. Examples of ODDFs include orally disintegrating tablets, capsules and rapidly dissolving films and wafers.

Extended release dosage forms (ERDFs) have extended release profiles and are those that allow a reduction in dosing frequency as compared to that presented by a conventional dosage form, e.g., a solution or unmodified release dosage form. ERDFs provide a sustained duration of action of a drug. Suitable formulations which provide extended release profiles are well-known in the art. For example, coated slow release beads or granules ("beads" and "granules" are used interchangeably herein) in which one or more of dextromethorphan or a pharmaceutically acceptable salt thereof, a CYP2D6 enzyme inhibitor and/or a CYP3A4 enzyme inhibitor is applied to beads, e.g., confectioners nonpareil beads, and then coated with conventional release retarding materials such as waxes, enteric coatings and the like. In embodiments, beads can be formed in which one or more of dextromethorphan or a pharmaceutically acceptable salt thereof, a CYP2D6 enzyme inhibitor and/or a CYP3A4 enzyme inhibitor is mixed with a material to provide a mass from which the drug leaches out. In embodiments, the beads may be engineered to provide different rates of release by varying characteristics of the coating or mass, e.g., thickness, porosity, using different materials, etc. Beads having different rates of release may be combined into a single dosage form to provide variable or continuous release. The beads can be contained in capsules or compressed into tablets.

Extended release liquids release medications slowly. For example, resins incorporating drugs can be suspended in liquid vehicles which slowly release medications into the body. In embodiments, one or more of dextromethorphan or a pharmaceutically acceptable salt thereof, a CYP2D6 enzyme inhibitor and/or a CYP3A4 enzyme inhibitor are incorporated into an ion-exchange polymer such as polistirex which is formed by the reaction of styrene monomers. Such polymers may be used as an extended-release matrix in pharmaceutical preparations, including medications like dextromethorphan, where it can provide a gradual and sustained release of active ingredients over time. See, e.g., U.S. Pat. No. 4,785,055 and a commercially available product, i.e., Delsym®. The exact composition and structure of polistirex can vary based on the specific manufacturing process and intended application. Polistirex is a type of polystyrene, which is a synthetic polymer composed of repeating units of styrene molecules, the chemical structure of which is $CH_2=CHC_6H_5$. This structure repeats along the polymer chain to form a polystyrene polymer. The polymerization process can involve various catalysts and conditions, leading to different molecular weights and properties of the resulting polistirex polymer. In the context of extended-release medications such as Delsym®, dextromethorphan polistirex is created by association of dextromethorphan to the polistirex matrix. The gradual release of dextromethorphan from the polistirex matrix allows for resistance to its rapid degradation and a prolonged effect of the medication.

In embodiments, modified dosage forms herein incorporate delayed release dosage forms having delayed release profiles. Delayed release dosage forms can include delayed release tablets or delayed release capsules. A delayed release tablet is a solid dosage form which releases a drug (or drugs) such one or more of dextromethorphan or a pharmaceutically acceptable salt thereof, a CYP2D6 enzyme inhibitor and/or a CYP3A4 enzyme inhibitor at a time other than promptly after administration. In this manner, dextromethorphan or a pharmaceutically acceptable salt thereof can be made to release first while one or both of the enzyme inhibitors are made to have delayed release. Alternatively, one or both of the enzyme inhibitors can be made to release first while dextromethorphan or a pharmaceutically acceptable salt thereof is made to have delayed release. A delayed release capsule is a solid dosage form in which the drug is enclosed within either a hard or soft soluble container made from a suitable form of gelatin, and which releases a drug (or drugs) at a time other than promptly after administration. For example, enteric-coated tablets, capsules, particles and beads are well-known examples of delayed release dosage forms. Enteric coated tablets, capsules and particles and beads pass through the stomach and release the drug in the intestine. In embodiments, a delayed release tablet is a solid dosage form containing a conglomerate of medicinal particles that releases a drug (or drugs) at a time other than promptly after administration. In embodiments, the conglomerate of medicinal particles is covered with a coating which delays release of the drug. In embodiments, a delayed release capsule is a solid dosage form containing a conglomerate of medicinal particles that releases a drug (or drugs) at a time other than promptly after administration. In embodiments, the conglomerate of medicinal particles is covered with a coating which delays release of the drug.

Delayed release dosage forms are known to those skilled in the art. For example, coated delayed release beads or granules in which one or more of dextromethorphan or a pharmaceutically acceptable salt thereof, a CYP2D6 enzyme inhibitor and/or a CYP3A4 enzyme inhibitor is applied to beads, e.g., confectioners nonpareil beads, and then coated with conventional release delaying materials such as waxes, enteric coatings and the like. In embodiments, beads can be formed in which one or more of dextromethorphan or a pharmaceutically acceptable salt thereof, a CYP2D6 enzyme inhibitor and/or a CYP3A4 enzyme inhibitor is mixed with a material to provide a mass from which the drug leaches out. In embodiments, the beads may be engineered to provide different rates of release by varying characteristics of the coating or mass, e.g., thickness, porosity, using different materials, etc. In embodiments, enteric coated granules of one or more of dextromethorphan or a pharmaceutically acceptable salt thereof, a CYP2D6 enzyme inhibitor and/or a CYP3A4 enzyme inhibitor can be contained in an enterically coated capsule or tablet which releases the granules in the small intestine. In embodiments, the granules have a coating which remains intact until the coated granules reach at least the ileum and thereafter provide a delayed release of the drug in the colon. Suitable enteric coating materials are well known in the art, e.g., Eudragit® coatings such methacrylic acid and methyl methacrylate polymers and others. The granules can be contained in capsules or compressed into tablets.

In embodiments, one or more of dextromethorphan or a pharmaceutically acceptable salt thereof, a CYP2D6 enzyme inhibitor and/or a CYP3A4 enzyme inhibitor is incorporated into porous inert carriers that provide delayed release profiles. In embodiments, the porous inert carriers incorporate channels or passages from which the drug diffuses into surrounding fluids. In embodiments, one or more of dextromethorphan or a pharmaceutically acceptable salt thereof, a CYP2D6 enzyme inhibitor and/or a CYP3A4 enzyme inhibitor is incorporated into an ion-exchange resin to provide a delayed release profile. Delayed action may result from a predetermined rate of release of the drug from the resin when the drug-resin complex contacts gastrointestinal fluids and the ionic constituents dissolved therein. In embodiments, membranes are utilized to control rate of release from drug containing reservoirs. In embodiments, liquid preparations may also be utilized to provide a delayed release profile. For example, a liquid preparation consisting of solid particles dispersed throughout a liquid phase in which the particles are not soluble. The suspension is formulated to allow at least a reduction in dosing frequency as compared to that drug presented as a conventional dosage form (e.g., as a solution or a prompt drug-releasing, conventional solid dosage form). For example, a suspension of ion-exchange resin constituents or microbeads.

In embodiments, transdermal pharmaceutical formulations are provided for treatment of pain. Transdermal formulations may encompass dosage forms of gels, ointments, lotions, sprays, or patches. Transdermal formulations such as patches rely for their effect on delivery of a known flux of drug to the skin for a prolonged period of time, generally a day, several days, or a week. Two mechanisms may be used to regulate drug flux: either the drug is contained within a drug reservoir, which is separated from the skin of the wearer by a synthetic membrane, through which the drug diffuses; or the drug is held dissolved or suspended in a polymer matrix, through which the drug diffuses to the skin. In embodiments, transdermal pharmaceutical formulations herein are formulated to provide maximum thermodynamic driving force for passive diffusion across the skin which is saturated with sufficient payload of one or more of dextromethorphan or a pharmaceutically acceptable salt thereof, a CYP2D6 enzyme inhibitor and/or a CYP3A4 enzyme inhibitor to insure delivery across the skin. In delivery systems involving transdermal patches, one or more of dextromethorphan or a pharmaceutically acceptable salt thereof, a CYP2D6 enzyme inhibitor and/or a CYP3A4 enzyme inhibitor is stored, e.g., in a reservoir (reservoir type) or dissolved in a liquid or gel-based reservoir (matrix type).

In embodiments, transdermal formulations may include chemical penetration enhancers and emulsions to facilitate transport of one or more of dextromethorphan or a pharmaceutically acceptable salt thereof, a CYP2D6 enzyme inhibitor and/or a CYP3A4 enzyme inhibitor across the stratum corneum. Examples of suitable penetration enhancers are alcohols, sulphoxides, azone, pyrrolidones, essential oils, terpenes and terpenoids, fatty acids, water and urea. In embodiments, semisolid vehicles such as proniosomes and microemulsion gels may be utilized as penetration enhancers. Proniosomes are non-ionic based surfactant vesicles and may be known as "dry niosomes" since they can require hydration before drug release and permeation through the skin. Upon hydration proniosomes are converted into niosomes which are capable of diffusing across the stratum corneum and then adhere to the cell surface which causes a high thermodynamic activity gradient of the drug at the vesicle/stratum corneum surface, thus acting as the driving force for the penetration of drugs across the skin.

The starting point for the evaluation of the kinetics of drug release from a transdermal patch is an estimation of the drug compound's maximum flux across the skin (flux (J)) which is typically expressed in units of $g/cm^2/h$). Based on Fick's law of diffusion, the transport of one or more of dextromethorphan or a pharmaceutically acceptable salt thereof, a CYP2D6 enzyme inhibitor and/or a CYP3A4 enzyme inhibitor molecules across skin will be maintained until the concentration gradient ceases to exist.

Accordingly, transdermal pharmaceutical formulations incorporating a reservoir will deliver a steady flux of one or more of dextromethorphan or a pharmaceutically acceptable salt thereof, a CYP2D6 enzyme inhibitor and/or a CYP3A4 enzyme inhibitor across the membrane as long as excess undissolved drug remains in the reservoir. The time required for one or more of dextromethorphan or a pharmaceutically acceptable salt thereof, a CYP2D6 enzyme inhibitor and/or a CYP3A4 enzyme inhibitor to reach a steady state of diffusion is called the lag time. In embodiments, matrix or monolithic devices may be characterized by a falling drug flux with time, as the matrix layers closer to the skin are depleted of drug. In embodiments, reservoir patches can include a porous membrane covering the reservoir of medication which can control release, while heat melting thin layers of medication embedded in the polymer matrix (e.g., the adhesive layer), can control release of drug from matrix or monolithic devices.

In embodiments, transdermal patches can include a release liner which protects the patch during storage and is removed prior to use, drug or drug solution in direct contact with the release liner, an adhesive which serves to adhere the components of the patch together along with adhering the patch to the skin, one or more membranes which can separate other layers, control the release of the drug from the reservoir and multi-layer patches, etc., and backing which protects the patch from the outer environment.

In embodiments, transdermal patches may include, but are not limited to, single-layer drug-in-adhesive patches, wherein the adhesive layer contains one or more of dextromethorphan or a pharmaceutically acceptable salt thereof, a CYP2D6 enzyme inhibitor and/or a CYP3A4 enzyme inhibitor and serves to adhere the various layers of the patch together, along with the entire patch system to the skin, but is also responsible for the releasing of the drug; multi-layer drug-in-adhesive, wherein which is similar to a single-layer drug-in-adhesive patch, but contains multiple layers, for example, a layer for immediate release of the drug and another layer for controlled release of drug from the reservoir; reservoir patches wherein the drug layer is a liquid compartment containing a drug solution or suspension separated by the adhesive layer; matrix patches, wherein a drug layer of a semisolid matrix containing a drug solution or suspension which is surrounded and partially overlaid by the adhesive layer; and vapor patches, wherein an adhesive layer not only serves to adhere the various layers together but also to release vapor. Methods for making transdermal patches are described, e.g., in U.S. Pat. Nos. 6,461,644, 6,676,961, 5,985,311, and 5,948,433.

For example, an exemplary patch can include an impermeable backing bonded about its periphery to a permeation enhancer release rate controlling element and spaced apart therefrom in its central portion to define a permeation enhancer reservoir. The permeation enhancer release rate controlling element is similarly bonded about its periphery to a porous support member and spaced apart therefrom in its central portion to define an aqueous drug reservoir containing one or more of dextromethorphan or a pharmaceutically acceptable salt thereof, a CYP2D6 enzyme inhibitor and/or a CYP3A4 enzyme inhibitor, which is water soluble. A contact adhesive layer which is permeable to the one or more of dextromethorphan or a pharmaceutically acceptable salt thereof, a CYP2D6 enzyme inhibitor and/or a CYP3A4 enzyme inhibitor and enhancer can be bonded to the surface of porous support and a strippable release liner, adapted to protect the adhesive prior to use and can be readily removed therefrom, may also be provided. To permit transport of drug and enhancer to the skin, the adhesive may be porous or hydrated to be permeable to the drug and enhancer. If impermeable to drug and enhancer, the adhesive can be located or otherwise adapted to impose no significant resistance to drug and permeation enhancer transport to the skin. In embodiments, a porous polyacrylate adhesive can be utilized in the contact adhesive layer. If a hydratable contact adhesive formulation is used, the adhesive can be equilibrated with at least about 10 weight percent water to permit transport of ionized drug. It should be recognized, however, that if a peripherally located adhesive is used, it need not be porous or permeable. Also, if desired, an adhesive overlay or some other means such as buckles, belts, or elastic bands could be used to maintain the transdermal delivery device on the skin in which case, if properly packaged, the adhesive layer and the strippable release liner could be omitted. Such a system might be desirable, for example, if the drug adversely affected the adhesive properties of the adhesive layer or if the drug were highly soluble in the adhesive.

In embodiments, the aqueous reservoir containing the one or more of dextromethorphan or a pharmaceutically acceptable salt thereof, a CYP2D6 enzyme inhibitor and/or a CYP3A4 enzyme inhibitor dispersed therein can contain at least 50%, e.g., 55%, 60%, 65%, 70%, 75%, 80%, 85% or 90%, water. In embodiments, the one or more of dextromethorphan or a pharmaceutically acceptable salt thereof, a CYP2D6 enzyme inhibitor and/or a CYP3A4 enzyme inhibitor is present at a level above saturation. In embodiments, the reservoir can be in the form of a gel which may also contain stabilizing agents, other excipients and additives. A buffering agent may also be present if required to maintain the drug reservoir at physiological pH.

The permeation enhancer release rate controlling membrane controls the rate of release of the permeation enhancer from the permeation enhancer reservoir to the skin. In embodiments, a porous substrate functions as a physical support for the gelled aqueous reservoir and it should be sufficiently porous so that it imposes little or no resistance to the transport of drug and permeation enhancer to the skin. In this regard, viscosity of the aqueous reservoir can be related to the porosity of the porous substrate, i.e., it should be sufficiently viscous so that the aqueous reservoir will not readily flow through the porous substrate. The amount of gelling or other thickening agent used is not critical but should be an amount required to produce a viscosity in the aqueous reservoir sufficient to prevent the reservoir from migrating or otherwise leaking or oozing through the porous substrate. The porous adhesive is likewise selected to provide little or no resistance to drug or enhancer release. A function of the porous substrate is to provide a support to which the adhesive can be applied since it is difficult in many cases to provide a good bond between the porous adhesive and the aqueous medium within the reservoir. In embodiments, the rate controlling membrane can be a hydrophobic membrane which is capable of controlling the rate of release of the permeation enhancer from the enhancer reservoir while simultaneously preventing either water or the drug from diffusing or otherwise migrating into enhancer reservoir. In embodiments, upon standing, the aqueous drug reservoir can contain a saturation level of the permeation enhancer.

The impermeable backing can be any material which has the desired flexibility, impermeability and insolubility with respect to the permeation enhancer and may, e.g., either be a single element or a metalized or composite coated element. Suitable materials can include, without limitation, ethylene vinyl acetate copolymers (EVA), polyesters, metalized polyesters, polyethylenes, polycarbonates, polyvinyl chlorides, polyvinylidene fluoride, polysulfones, or laminates of the above such as metalized polyester/EVA or medium density polyethylene/EVA.

In embodiments, the porous substrate can be a soft, open-mesh, hydrophobic, fibrous material or may also be a non-fibrous, porous or sponge-like material as long as the substrate performs the function of being bondable to the adhesive and maintaining the gelled aqueous material within the reservoir without providing any significant resistance to the transport of drug and permeation enhancer. Examples of suitable materials include spun laced polyester, spun-laced polyolefin coated polyester, spun bonded polyethylene, spun laced polyethylene or EVA, microporous polypropylene, microporous polycarbonate, woven nylon, rayon or polyester cloths, and open cellular polyethylene or polyurethane foams.

The porous adhesive can be, e.g., a polyacrylate contact adhesive or any other suitable porous adhesive. Alternatively, the adhesive can be a non-porous contact adhesive which is applied about the periphery leaving the center portion beneath the aqueous reservoir substantially free of adhesive. In that case, any biocompatible contact adhesive could be applied, porous or not. Examples of adhesive compositions include silicone adhesives, polyacrylates, polyisobutylene-mineral oil adhesives, tackified styrene-isoprene-styrene block copolymers (SIS), tackified EVA contact adhesives, polyacrylamides and various hydratable, hot melt or emulsified (water borne) adhesive compositions.

The strippable release liner can be any material known to the art and may be the same as or different from the material used to provide the impermeable backing. A basic requirement for the strippable release liner is that it be substantially impermeable to the passage of components from the reservoir and be readily removed from the adhesive without destruction of the integrity of the patch.

With respect to the gelled aqueous drug reservoir, in the case of one or more of dextromethorphan or a pharmaceutically acceptable salt thereof, a CYP2D6 enzyme inhibitor and/or a CYP3A4 enzyme inhibitor, in embodiments, water is the continuous phase. For that reason, the reservoir should be at least 50%, e.g., over 70% water. The gelling agent used to thicken the reservoir can be any of a wide variety of gelling agents, such as silica, particulate porous polyisoprene, bentonite clay, various gums such as agar, tragacanth, polysaccharides, cellulosic materials such as hydroxyethyl cellulose, hydroxypropyl cellulose or hydroxypropyl methyl cellulose and polyacrylates. The basic requirements are that the gelling agent is non-reactive with one or more of dextromethorphan or a pharmaceutically acceptable salt thereof, a CYP2D6 enzyme inhibitor and/or a CYP3A4 enzyme inhibitor and does not substantially interfere with the ready diffusion of the materials from the patch. A relatively wide degree of flexibility in the amount of gelling agent used is available since the required viscosity varies inversely with the pore size selected for the substrate. A general range of approximately 1% to 10% by weight of these gelling agents may be adequate.

The drug reservoir may also contain a buffer to maintain the pH of the solution in a desired range during the drug delivery period. Suitable buffers should, of course, be unreactive with the other components of the system. Suitable buffers for acid drugs and basic drugs include, without limitation, phosphates, citrates, ascorbates and carbonates.

The permeation enhancer release rate controlling membrane should be substantially impermeable to the flow of water and one or more of dextromethorphan or a pharmaceutically acceptable salt thereof, a CYP2D6 enzyme inhibitor and/or a CYP3A4 enzyme inhibitor from the aqueous reservoir into the permeation enhancer reservoir while having a sufficient degree of permeability to the permeation enhancer to permit the rate at which the permeation enhancer is released from the permeation enhancer reservoir into the skin to be controlled by membranes of reasonable thickness, e.g., in the range of 0.001-0.003 inches. The permeation enhancer release rate controlling membrane may either be a solid membrane or a microporous membrane having rate controlling material in the micropores to meter the release of permeation enhancer. Examples of rate controlling materials for the formation of a membrane per se or for the rate controlling material to be included in the pores of a microporous membrane can be, e.g., hydrophobic materials such as polyethylene EVA, polycarbonates, polyvinyl chloride, polyacrylate polymers, polysulfone polymers, polyvinylidienes, polyvinylidenes, polyesters, and polyisobutylenes.

The permeation enhancer may be present in the permeation enhancer reservoir either neat or as solution or dispersion in an appropriate medium. Exemplary materials include surfactants, such as alkyl substituted sulfoxides, e.g., n-octyl methyl sulfoxide, n-nonyl methyl sulfoxide, n-decylmethyl sulfoxide (n-DMS), n-undecyl methyl sulfoxide, n-dodecyl methyl sulfoxide; mono- and di-substituted alkyl polyethylene glycols such as polyethylene glycol mono laurate and polyethylene glycol di laurate; ethanol and other lower alcohols; n-methyl pyrrolidone, dimethyl lauramine, diethyltoluamide, and the 1-substituted azacycloalkan-2-ones.

In embodiments, active methods are utilized to drive penetration of one or more of dextromethorphan or a pharmaceutically acceptable salt thereof, a CYP2D6 enzyme inhibitor and/or a CYP3A4 enzyme inhibitor through the stratum corneum. In embodiments, active methods for skin permeabilization involve the use of external energy to act as a driving force for drug transport across the skin or by physically disrupting the stratum corneum. Active methods for skin permeabilization include ultrasound, electrically assisted methods (electroporation and iontophoresis), velocity based devices (powder injection, jet injectors), thermal approaches (lasers and radio-frequency heating) and mechanical methodologies such as microneedles and tape stripping.

In embodiments, pharmaceutical compositions described herein are suitable for parenteral administration, including, e.g., intramuscular (i.m.), intravenous (i.v.), subcutaneous (s.c.), intraperitoneal (i.p.), epidural, or intrathecal (i.t.). Parenteral compositions should be sterile for administration by injection, infusion or implantation into the body and may be packaged in either single-dose or multi-dose containers. In embodiments, liquid pharmaceutical compositions for parenteral administration to a subject include an active substance, e.g., one or more of dextromethorphan or a pharmaceutically acceptable salt thereof, a CYP2D6 enzyme inhibitor and/or a CYP3A4 enzyme inhibitor in any of the respective amounts described above. In embodiments, the pharmaceutical compositions for parenteral administration are formulated as a total volume of about, e.g., 10 ml, 20 ml, 25 ml, 50 ml, 100 ml, 200 ml, 250 ml, or 500 ml. In embodiments, the compositions are contained in a bag, a glass vial, a plastic vial, or a bottle.

Pharmaceutical compositions for parenteral administration provided herein may include one or more excipients, e.g., solvents, solubility enhancers, suspending agents, buffering agents, isotonicity agents, stabilizers or antimicrobial preservatives. When used, the excipients of the parenteral compositions will not adversely affect the stability, bioavailability, safety, and/or efficacy of one or more of dextromethorphan or a pharmaceutically acceptable salt thereof, a CYP2D6 enzyme inhibitor and/or a CYP3A4 enzyme inhibitor used in the composition. Thus, parenteral compositions are provided wherein there is no incompatibility between any of the components of the dosage form.

In embodiments, parenteral compositions containing one or more of dextromethorphan or a pharmaceutically acceptable salt thereof, a CYP2D6 enzyme inhibitor and/or a CYP3A4 enzyme inhibitor include a stabilizing amount of at least one excipient. For example, excipients may be selected from the group consisting of buffering agents, solubilizing agents, tonicity agents, antioxidants, chelating agents, antimicrobial agents, and preservative. One skilled in the art will appreciate that an excipient may have more than one function and be classified in one or more defined group.

It should be understood that the dosage amounts of dextromethorphan or a pharmaceutically acceptable salt thereof, a CYP2D6 enzyme inhibitor and a CYP3A4 enzyme inhibitor that are provided herein are applicable to all the dosage forms described herein including conventional dosage forms, modified dosage forms, as well as the parenteral formulations described herein. Those skilled in the art will determine appropriate amounts depending on criteria such as dosage form, route of administration, subject tolerance, efficacy, therapeutic goal and therapeutic benefit, among other pharmaceutically acceptable criteria. It should be understood that dextromethorphan or a pharmaceutically acceptable salt thereof, a CYP2D6 enzyme inhibitor and a CYP3A4 enzyme inhibitor need not be given together or even in the same form. For example, the dextromethorphan can be given parenterally and the other compounds by mouth—or the other way around.

Clinical efficacy of treatment can be monitored using any method known in the art. Measurable parameters to monitor efficacy will depend on the condition being treated. For monitoring the status or improvement of pain, various pain assessment scales and tools are known. For example, the numeric pain rating scale (NRS), typically ranging from one to ten with one being the least severe and 10 being the most severe, can be used. Another example is the visual analogue scale (VAS), which is a measurement instrument that tries to measure a characteristic or attitude that is believed to range across a continuum of values and cannot easily be directly measured. For example, the amount of pain that a patient feels ranges across a continuum from none to an extreme amount of pain.

Unless defined otherwise, all technical and scientific terms used herein have the same meanings as commonly understood by one of skill in the art to which the disclosure herein belongs.

The term "about" or "approximately" as used herein means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, up to 10%, up to 5%, and/or up to 1% of a given value.

"Improvement" refers to the treatment of pain and is discernable, either subjectively by a subject or objectively by an observer, for a period of time, e.g., 2 hours, 3 hours, 4 hours, 5 hours, 6 hours, 12 hours, 24 hours, etc. after waking.

"Treating", "treatment" or "treat" can refer to the following: reducing, improving, relieving, ameliorating, mitigating, inhibiting, reversing and/or alleviating pain in a subject, or delaying the appearance pain (prophylaxis) in a subject. In embodiments, "treating", "treat" or "treatment" may refer to preventing the appearance of clinical symptoms of a disease or condition in a subject that may be afflicted with or predisposed to the disease or condition, but does not yet experience or display clinical or subclinical symptoms of the disease or condition. "Treating", "treat" or "treatment" also refers to inhibiting or relieving pain. The benefit to a subject to be treated may be statistically significant, mathematically significant, or at least perceptible to the subject and/or the physician. Nonetheless, prophylactic (preventive) and therapeutic (curative) treatment are two separate embodiments of the disclosure herein.

"Pharmaceutically acceptable" refers to molecular entities and compositions that are "generally regarded as safe", e.g., that are physiologically tolerable and do not typically produce an allergic or similar untoward reaction, such as gastric upset and the like, when administered to a human. In embodiments, this term refers to molecular entities and compositions approved by a regulatory agency of the federal or a state government, as the GRAS list under section 204(s) and 409 of the Federal Food, Drug and Cosmetic Act, that is subject to premarket review and approval by the FDA or similar lists, the U.S. Pharmacopeia or another generally recognized pharmacopeia for use in animals, and more particularly in humans.

"Subject in need thereof" includes individuals that are in pain. The methods and compositions including one or more of dextromethorphan or a pharmaceutically acceptable salt thereof, a CYP2D6 enzyme inhibitor and a CYP3A4 enzyme inhibitor may be provided to any individual including, e.g., wherein the subject is a neonate, infant, a pediatric subject (6 months to 12 years), an adolescent subject (age 12-18 years) or an adult (over 18 years). Subjects include mammals such as humans. "Patient" and "subject" may be used interchangeably herein.

The term "pharmaceutically acceptable salt", as used herein, refers to derivatives of the compounds defined herein, wherein the parent compound is modified by making acid or base salts thereof. Examples of pharmaceutically acceptable salts include but are not limited to mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include but are not limited to those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, naphthalenesulfonic, methanesulfonic, ethane disulfonic, oxalic, and isethionic salts. The pharmaceutically acceptable salts can be synthesized from the parent compound, which contains a basic or acidic moiety, by conventional chemical methods.

The following examples are included to help illustrate and/or augment the description herein. The examples are not to be construed as limiting the disclosure herein in any way.

EXAMPLES

Comparative Example 1

Subject is a 75 year old female with past medical history significant for traumatic amputation of partial thumb and four fingers of the right hand at age 3, severe constant left arm and shoulder pain dating from 1971, chronic depression, anxiety, seizure disorder, narcolepsy, chronic opioid use since at least 1975, subdural hematoma, multiple prior spinal surgeries, post-surgical fixation and hardware insertion C5-sacrum; dysphagia/post-surgical inflammatory pharyngeal mass, s/p pharyngeal mass biopsy ENT and C3-C6 plate removal by neurosurgery, history of aspiration pneumonia requiring PEG tube feedings now back to oral feeds, shoulder fracture requiring operative repair, s/p spine surgery for washout and hardware removal. Subject had long standing (>20 years) grade #8-9 upper extremity pain not relieved by a strong opioid regimen: hydromorphone 16 mg every 6 hours.

Dextromethorphan polystyrex (Delsym®) 30 mg every AM given in conjunction with 50 mg quinidine orally every 6 hours in addition to hydromorphone 16 mg every 6 hours produced near complete pain relief in the subject's upper extremity pain that was not relieved by the hydromorphone given alone. Relief from added dextromethorphan/quinidine lasted for 1-3 weeks, then abruptly was ineffective. However, when dextromethorphan was terminated for 6 months, its potency returned, but again, only for 1-3 weeks. This sequence of events repeated itself for over seven years in this subject.

Example 1

Subject is a 75 year old female with past medical history significant for traumatic amputation of partial thumb and four fingers of the right hand at age 3, severe constant left arm and shoulder pain dating from 1971, chronic depression, anxiety, seizure disorder, narcolepsy, chronic opioid use since at least 1975, subdural hematoma, multiple prior spinal surgeries, post-surgical fixation and hardware insertion C5-sacrum; dysphagia/post-surgical inflammatory pharyngeal mass, s/p pharyngeal mass biopsy ENT and C3-C6 plate removal by neurosurgery, history of aspiration pneumonia requiring PEG tube feedings now back to oral feeds, shoulder fracture requiring operative repair, s/p spine surgery for washout and hardware removal. Subject had long standing (>20 years) grade #8-9 upper extremity pain not relieved by a strong opioid regimen: hydromorphone 16 mg every 6 hours.

Starting in 2015, the subject was treated with dextromethorphan polystyrex (Delsym®) 30 mg every AM given in conjunction with 50 mg quinidine orally every 6 hours and hydromorphone 16 mg every 6 hours. Relief from dextromethorphan/quinidine, hydromorphone lasted for 1-3 weeks, then abruptly was ineffective. Dextromethorphan was terminated for 6 months, its potency returned but again, only for 1-3 weeks. This sequence of events had repeated itself for over seven years in this subject.

Beginning in March, 2022, the subject was administered 4-8 ounces of grapefruit juice (which contains the CYP3A4 enzyme inhibitor 6'7' dihydrobergamottin −5 mg) with each dose of dextromethorphan/quinidine. As of September 2022, the subject reported markedly reduced pain and has consistently remained so since late March 2022.

While embodiments of the disclosure have been described and exemplified herein, it is not intended that the disclosure be limited thereto, as it is intended that the disclosure be as broad in scope as the art will allow and that the specification be read likewise. Therefore, the above description should not be construed as limiting, but merely as exemplifications of various embodiments. Those skilled in the art will envision other modifications within the scope and spirit of the claims appended hereto.

What is claimed is:

1. A method for treatment of pain comprising administering to a patient in need thereof dextromethorphan or a pharmaceutically acceptable salt thereof in combination with a CYP2D6 inhibitor and a CYP3A4 enzyme inhibitor, wherein the CYP2D6 inhibitor is selected from the group consisting of quinidine, quinine, ajmaline, amiodarone, bupropion, cannabidiol, celecoxib, chlorphenamine, chlorpromazine, cimetidine, cinacalcet, citalopram, clemastine, clomipramine, cocaine, diphenhydramine, doxepin, doxorubicin, duloxetine, escitalopram, fluoxetine, halofantrine, haloperidol, hydroxyzine, hyperforinkava, levomepromazine, lobeline, methadone, methylphenidate, metoclopramide, mibefradil, midodrine, niacin, niacinamide, *Nelumbo nucifera*, nuciferine, n-nornuciferine, 2-hydroxy-1-methoxyaporphine, omeprazole, paroxetine, perphenazine, promethazine, ranitidine, risperidone, ritonavir, sertraline, St. John's Wort, terbinafine, thioridazine, ticlopidine, tripelennamine, yohimbine and zuclopenthixol, and the CYP3A4 inhibitor is selected from the group consisting of amiodarone, aprepitant, atazanavir, bergamottin, 6'7' dihydoxybergamottin, cafestol, cannabidiol, chloramphenicol, cimetidine, ciprofloxacin, clarithromycin, cobicistat, darunavir, delavirdine, diltiazem, dithiocarbamate, domperidone, erythromycin, esomeprazole, fluconazole, fluvoxamine, gestodene, *Ginkgo biloba*, grapefruit juice, imatinib, indinavir, isoniazid, itraconazole, kava, ketoconazole, lopinavir, mibefradil, mifepristone, milk thistle, myricetin, nefazodone, nelfinavir, niacin, niacinamide, nilutamide, norfloxacin, omeprazole, orphenadrine, pantoprazole, piperine, quercetin, ranitidine, ritonavir, saquinavir, seproxetine, star fruit, teliromycin, tipranavir, valerian, valproic acid, verapamil and voriconazole.

2. The method for treatment of pain according to claim 1, wherein the dextromethorphan is dextromethorphan hydrobromide.

3. The method for treatment of pain according to claim 1, wherein the dextromethorphan is dextromethorphan polistirex.

4. The method for treatment of pain according to claim 1, wherein the dextromethorphan in combination with a CYP2D6 inhibitor and a CYP3A4 enzyme inhibitor is administered enterally.

5. The method for treatment of pain according to claim 4, wherein the dextromethorphan in combination with a CYP2D6 inhibitor and a CYP3A4 enzyme inhibitor is administered orally, sublingually, buccally, transdermally or rectally.

6. The method for treatment of pain according to claim 1, wherein the dextromethorphan in combination with a CYP2D6 inhibitor and a CYP3A4 enzyme inhibitor is administered parenterally.

7. The method for treatment of pain according to claim 1, wherein one or more of the dextromethorphan, CYP2D6 inhibitor and CYP3A4 enzyme inhibitor is administered in the form of a liquid, a tablet, a capsule, a caplet, a pill, an oral liquid, a lozenge, a film, a powder, an aerosol, or a patch.

8. The method for treatment of pain according to claim 1, wherein one or more of the dextromethorphan, CYP2D6 inhibitor and CYP3A4 enzyme inhibitor is administered as an extended release dosage form.

9. The method for treatment of pain according to claim 1, wherein one or more of the dextromethorphan, CYP2D6 inhibitor and CYP3A4 enzyme inhibitor is administered as an instant release dosage form.

10. The method for treatment of pain according to claim 1, wherein one or more of the dextromethorphan, CYP2D6 inhibitor and CYP3A4 enzyme inhibitor is administered as a delayed release dosage form.

11. The method for treatment of pain according to claim 1, wherein the pain is neuropathic pain.

12. The method for treatment of pain according to claim 1, wherein the pain is nociceptive pain.

13. The method for treatment of pain according to claim 1, wherein the pain is psychogenic pain.

14. The method for treatment of pain according to claim 1, wherein the pain is chronic pain.

15. The method for treatment of pain according to claim 1, wherein the pain is intractable pain.

16. The method for treatment of pain according to claim 1, wherein the pain is breakthrough pain.

17. The method for treatment of pain according to claim 1, wherein the dextromethorphan is administered at a dose ranging from about 10 mg to about 100 mg.

18. The method for treatment of pain according to claim 1, wherein the dextromethorphan is administered at a dose ranging from about 30 mg to about 60 mg.

19. The method for treatment of pain according to claim 1, wherein one or more of the dextromethorphan, CYP2D6 inhibitor and CYP3A4 enzyme inhibitor is administered from one to four times daily.

20. The method for treatment of pain according to claim 1, wherein the quinidine is administered in an amount ranging from about 25 mg to about 50 mg.

21. The method for treatment of pain according to claim 1, wherein the 6'7' dihydoxybergamottin is administered in an amount ranging from about 1 mg to about 10 mg.

22. The method for treatment of pain according to claim 19, wherein about 5 mg of 6'7' dihydoxybergamottin is administered.

23. The method for treatment of pain according to claim 1, wherein the dextromethorphan or a pharmaceutically acceptable salt thereof in combination with a CYP2D6 inhibitor and a CYP3A4 enzyme inhibitor is co-administered with an NMDA receptor antagonist.

24. The method for treatment of pain according to claim 23, wherein the NMDA receptor antagonist is selected from the group consisting of amantadine, ketamine, esketamine, memantine, atomoxetine, agmatine, delucemine, dextrorphan, eliprodil, gabapentin and magnesium.

25. The method for treatment of pain according to claim 1, wherein the patient in need thereof has been diagnosed with sickle cell anemia.

26. A pharmaceutical composition comprising dextromethorphan or a pharmaceutically acceptable salt thereof, a CYP2D6 inhibitor and a CYP3A4 enzyme inhibitor, wherein the CYP2D6 inhibitor is selected from the group consisting of quinidine, quinine, ajmaline, amiodarone, bupropion, cannabidiol, celecoxib, chlorphenamine, chlorpromazine, cimetidine, cinacalcet, citalopram, clemastine, clomipramine, cocaine, diphenhydramine, doxepin, doxorubicin, duloxetine, escitalopram, fluoxetine, halofantrine, haloperidol, hydroxyzine, hyperforinkava, levomepromazine, lobeline, methadone, methylphenidate, metoclopramide, mibefradil, midodrine, niacin, niacinamide, *Nelumbo nucifera*, nuciferine, n-nornuciferine, 2-hydroxy-1-methoxyaporphine, omeprazole, paroxetine, perphenazine, promethazine, ranitidine, risperidone, ritonavir, sertraline, St. John's Wort, terbinafine, thioridazine, ticlopidine, tripelennamine, yohimbine and zuclopenthixol, and the CYP3A4 inhibitor is selected from the group consisting of amiodarone, aprepitant, atazanavir, bergamottin, 6'7' dihydoxybergamottin, cafestol, cannabidiol, chloramphenicol, cimetidine, ciprofloxacin, clarithromycin, cobicistat, darunavir, delavirdine, diltiazem, dithiocarbamate, domperidone, erythromycin, esomeprazole, fluconazole, fluvoxamine, gestodene, *Ginkgo biloba*, grapefruit juice, imatinib, indinavir, isoniazid, itraconazole, kava, ketoconazole, lopinavir, mibefradil, mifepristone, milk thistle, myricetin, nefazodone, nelfinavir, niacin, niacinamide, nilutamide, norfloxacin, omeprazole, orphenadrine, pantoprazole, piperine, quercetin, ranitidine, ritonavir, saquinavir, seproxetine, star fruit, teliromycin, tipranavir, valerian, valproic acid, verapamil and voriconazole.

27. The pharmaceutical composition of claim 26, further comprising an NMDA receptor antagonist.

28. The pharmaceutical composition of claim 27, wherein the NMDA receptor antagonist is selected from the group consisting of amantadine, ketamine, esketamine, memantine, atomoxetine, agmatine, delucemine, dextrorphan, eliprodil, gabapentin and magnesium.

29. A method of treating pain in a patient diagnosed with sickle cell anemia comprising administering to the patient dextromethorphan or a pharmaceutically acceptable salt thereof in combination with a CYP2D6 inhibitor and a CYP3A4 enzyme inhibitor, wherein the CYP2D6 inhibitor is selected from the group consisting of quinidine, quinine, ajmaline, amiodarone, bupropion, cannabidiol, celecoxib, chlorphenamine, chlorpromazine, cimetidine, cinacalcet, citalopram, clemastine, clomipramine, cocaine, diphenhydramine, doxepin, doxorubicin, duloxetine, escitalopram, fluoxetine, halofantrine, haloperidol, hydroxyzine, hyperforinkava, levomepromazine, lobeline, methadone, methylphenidate, metoclopramide, mibefradil, midodrine, niacin, niacinamide, *Nelumbo nucifera*, nuciferine, n-nornuciferine, 2-hydroxy-1-methoxyaporphine, omeprazole, paroxetine, perphenazine, promethazine, ranitidine, risperidone, ritonavir, sertraline, St. John's Wort, terbinafine, thioridazine, ticlopidine, tripelennamine, yohimbine and zuclopenthixol, and the CYP3A4 inhibitor is selected from the group consisting of amiodarone, aprepitant, atazanavir, bergamottin, 6'7' dihydoxybergamottin, cafestol, cannabidiol, chloramphenicol, cimetidine, ciprofloxacin, clarithromycin, cobicistat, darunavir, delavirdine, diltiazem, dithiocarbamate, domperidone, erythromycin, esomeprazole, fluconazole, fluvoxamine, gestodene, *Ginkgo biloba*, grapefruit juice, imatinib, indinavir, isoniazid, itraconazole, kava, ketoconazole, lopinavir, mibefradil, mifepristone, milk thistle, myricetin, nefazodone, nelfinavir, niacin, niacinamide, nilutamide, norfloxacin, omeprazole, orphenadrine, pantoprazole, piperine, quercetin, ranitidine, ritonavir, saguinavir, seproxetine, star fruit, teliromycin, tipranavir, valerian, valproic acid, verapamil and voriconazole.

\* \* \* \* \*